(12) United States Patent (10) Patent No.: US 9,332,979 B2
Sullivan et al. (45) Date of Patent: May 10, 2016

(54) TENSIONABLE KNOTLESS ACROMIOCLAVICULAR REPAIRS AND CONSTRUCTS

(75) Inventors: Derek C. Sullivan, Bonita Springs, FL (US); Allen E. Holowecky, Naples, FL (US); Thomas Dooney, Jr., Naples, FL (US); Peter J. Millett, Edwards, CO (US)

(73) Assignee: Arthrex, Inc., Naples, FL (US)

( * ) Notice: Subject to any disclaimer, the term of this patent is extended or adjusted under 35 U.S.C. 154(b) by 534 days.

(21) Appl. No.: 13/553,202

(22) Filed: Jul. 19, 2012

(65) Prior Publication Data

US 2013/0023929 A1  Jan. 24, 2013

Related U.S. Application Data

(60) Provisional application No. 61/510,727, filed on Jul. 22, 2011.

(51) Int. Cl.
  *A61B 17/04* (2006.01)
  *A61B 17/88* (2006.01)
  *A61B 17/06* (2006.01)

(52) U.S. Cl.
  CPC ......... *A61B 17/0401* (2013.01); *A61B 17/0485* (2013.01); *A61B 17/0487* (2013.01); *A61B 17/888* (2013.01); *A61B 17/0483* (2013.01); *A61B 2017/0404* (2013.01); *A61B 2017/0409* (2013.01); *A61B 2017/0414* (2013.01); *A61B 2017/0445* (2013.01); *A61B 2017/0456* (2013.01); *A61B 2017/0496* (2013.01); *A61B 2017/06185* (2013.01)

(58) Field of Classification Search
  CPC ........... A61B 17/0401; A61B 17/0417; A61B 2017/044; A61B 2017/0445
  USPC ........................ 606/232, 139, 145; 623/13.14
  See application file for complete search history.

(56) References Cited

U.S. PATENT DOCUMENTS

| | | |
|---|---|---|
| 3,176,316 A | 4/1965 | Bodell |
| 4,187,558 A | 2/1980 | Dahlen et al. |
| 4,301,551 A | 11/1981 | Dore et al. |
| 4,400,833 A | 8/1983 | Kurland |
| 4,776,851 A | 10/1988 | Bruchman et al. |
| 4,790,850 A | 12/1988 | Dunn et al. |
| 4,792,336 A | 12/1988 | Hlavacek et al. |
| 4,851,005 A | 7/1989 | Hunt et al. |
| 4,863,471 A | 9/1989 | Mansat |
| 4,917,700 A | 4/1990 | Aikins |
| 4,932,972 A | 6/1990 | Dunn et al. |
| 5,024,669 A | 6/1991 | Peterson et al. |

(Continued)

FOREIGN PATENT DOCUMENTS

| | | |
|---|---|---|
| DE | 299 10 202 U1 | 9/1999 |
| DE | 201 01 791 U1 | 6/2001 |

(Continued)

*Primary Examiner* — Ryan J Severson
*Assistant Examiner* — Anh Dang
(74) *Attorney, Agent, or Firm* — Blank Rome LLP

(57) ABSTRACT

Systems and methods for AC joint dislocation surgical repairs, without knot tying. The surgical systems include two fixation devices (for example, a button and an anchor) joined by strand of flexible material having a knotless, self-cinching, adjustable loop with two splices that attach to the two fixation devices. The knotless, adjustable loop/fixation devices allow for tensioning of the AC repair after the anchor implantation.

8 Claims, 18 Drawing Sheets

(56) References Cited

U.S. PATENT DOCUMENTS

| | | |
|---|---|---|
| 5,026,398 A | 6/1991 | May et al. |
| 5,129,902 A | 7/1992 | Goble et al. |
| 5,171,274 A | 12/1992 | Fluckiger et al. |
| 5,211,647 A | 5/1993 | Schmieding |
| 5,217,495 A | 6/1993 | Kaplan et al. |
| 5,263,984 A | 11/1993 | Li et al. |
| 5,266,075 A | 11/1993 | Clark et al. |
| 5,306,301 A | 4/1994 | Graf et al. |
| 5,320,626 A | 6/1994 | Schmieding |
| 5,397,357 A | 3/1995 | Schmieding et al. |
| 5,562,669 A | 10/1996 | McGuire |
| 5,575,819 A | 11/1996 | Amis |
| 5,628,756 A | 5/1997 | Barker et al. |
| 5,643,266 A | 7/1997 | Li |
| 5,645,588 A | 7/1997 | Graf et al. |
| 5,931,869 A | 8/1999 | Boucher et al. |
| 5,961,520 A | 10/1999 | Beck et al. |
| 5,964,764 A | 10/1999 | West, Jr. et al. |
| 6,056,752 A | 5/2000 | Roger |
| 6,099,530 A | 8/2000 | Simonian et al. |
| 6,099,568 A | 8/2000 | Simonian et al. |
| 6,110,207 A | 8/2000 | Eichhorn et al. |
| 6,159,234 A | 12/2000 | Bonutti et al. |
| 6,193,754 B1 | 2/2001 | Seedhom |
| 6,203,572 B1 | 3/2001 | Johnson et al. |
| 6,283,996 B1 | 9/2001 | Chervitz et al. |
| 6,296,659 B1 | 10/2001 | Foerster |
| 6,325,804 B1 | 12/2001 | Wenstrom et al. |
| 6,517,578 B2 | 2/2003 | Hein |
| 6,533,802 B2 | 3/2003 | Bojarski et al. |
| 7,097,654 B1 | 8/2006 | Freedland |
| 7,494,506 B2 | 2/2009 | Brulez et al. |
| 7,686,838 B2 | 3/2010 | Wolf et al. |
| 7,749,250 B2 | 7/2010 | Stone et al. |
| 7,776,039 B2 | 8/2010 | Bernstein et al. |
| 7,819,898 B2 | 10/2010 | Stone et al. |
| 7,828,855 B2 | 11/2010 | Ellis et al. |
| 7,875,057 B2 | 1/2011 | Cook et al. |
| 7,905,903 B2 | 3/2011 | Stone et al. |
| 7,914,539 B2 | 3/2011 | Stone et al. |
| 8,109,965 B2 | 2/2012 | Stone et al. |
| 8,118,836 B2 | 2/2012 | Denham et al. |
| 8,162,997 B2 | 4/2012 | Struhl |
| 8,206,446 B1 | 6/2012 | Montgomery |
| 8,231,654 B2 | 7/2012 | Kaiser et al. |
| 2001/0041938 A1 | 11/2001 | Hein |
| 2002/0161439 A1 | 10/2002 | Strobel et al. |
| 2003/0114929 A1 | 6/2003 | Knudsen et al. |
| 2004/0015171 A1 | 1/2004 | Bojarski et al. |
| 2004/0059415 A1 | 3/2004 | Schmieding |
| 2004/0073306 A1 | 4/2004 | Eichhorn et al. |
| 2004/0243235 A1 | 12/2004 | Goh et al. |
| 2004/0267360 A1 | 12/2004 | Huber |
| 2005/0004670 A1 | 1/2005 | Gebhardt et al. |
| 2005/0033363 A1 | 2/2005 | Bojarski et al. |
| 2005/0065533 A1 | 3/2005 | Magen et al. |
| 2005/0070906 A1 | 3/2005 | Clark et al. |
| 2005/0137704 A1 | 6/2005 | Steenlage |
| 2005/0149187 A1 | 7/2005 | Clark et al. |
| 2005/0171603 A1 | 8/2005 | Justin et al. |
| 2005/0203623 A1 | 9/2005 | Steiner et al. |
| 2005/0261766 A1 | 11/2005 | Chervitz et al. |
| 2006/0067971 A1 | 3/2006 | Story et al. |
| 2006/0095130 A1 | 5/2006 | Caborn et al. |
| 2006/0142769 A1 | 6/2006 | Collette |
| 2006/0265064 A1 | 11/2006 | Re et al. |
| 2007/0021839 A1 | 1/2007 | Lowe |
| 2007/0083236 A1 | 4/2007 | Sikora et al. |
| 2007/0118217 A1 | 5/2007 | Brulez et al. |
| 2007/0162123 A1 | 7/2007 | Whittaker et al. |
| 2007/0162125 A1 | 7/2007 | LeBeau et al. |
| 2007/0179531 A1 | 8/2007 | Thornes |
| 2007/0225805 A1 | 9/2007 | Schmieding |
| 2007/0239209 A1 | 10/2007 | Fallman |
| 2007/0239275 A1 | 10/2007 | Willobee |
| 2007/0250163 A1 | 10/2007 | Cassani |
| 2007/0270857 A1 | 11/2007 | Lombardo et al. |
| 2008/0046009 A1 | 2/2008 | Albertorio et al. |
| 2008/0177302 A1 | 7/2008 | Shurnas |
| 2008/0188935 A1 | 8/2008 | Saylor et al. |
| 2008/0188936 A1 | 8/2008 | Ball et al. |
| 2008/0208252 A1 | 8/2008 | Holmes |
| 2008/0215150 A1 | 9/2008 | Koob et al. |
| 2008/0228271 A1 | 9/2008 | Stone et al. |
| 2008/0234819 A1 | 9/2008 | Schmieding et al. |
| 2008/0243248 A1 | 10/2008 | Stone et al. |
| 2008/0275553 A1 | 11/2008 | Wolf et al. |
| 2008/0275554 A1 | 11/2008 | Iannarone et al. |
| 2008/0300683 A1 | 12/2008 | Altman et al. |
| 2008/0312689 A1 | 12/2008 | Denham et al. |
| 2009/0018581 A1* | 1/2009 | Anderson et al. .............. 606/232 |
| 2009/0018654 A1 | 1/2009 | Schmieding et al. |
| 2009/0030516 A1 | 1/2009 | Imbert |
| 2009/0054982 A1 | 2/2009 | Cimino |
| 2009/0062854 A1 | 3/2009 | Kaiser et al. |
| 2009/0082805 A1 | 3/2009 | Kaiser et al. |
| 2009/0187244 A1 | 7/2009 | Dross |
| 2009/0216326 A1 | 8/2009 | Hirpara et al. |
| 2009/0228017 A1 | 9/2009 | Collins |
| 2009/0234451 A1 | 9/2009 | Manderson |
| 2009/0265003 A1 | 10/2009 | Re et al. |
| 2009/0275950 A1 | 11/2009 | Sterrett et al. |
| 2009/0306776 A1 | 12/2009 | Murray |
| 2009/0306784 A1 | 12/2009 | Blum |
| 2009/0312776 A1 | 12/2009 | Kaiser et al. |
| 2010/0049258 A1 | 2/2010 | Dougherty |
| 2010/0049319 A1 | 2/2010 | Dougherty |
| 2010/0100182 A1 | 4/2010 | Barnes et al. |
| 2010/0145384 A1 | 6/2010 | Stone et al. |
| 2010/0145448 A1 | 6/2010 | Montes De Oca Balderas et al. |
| 2010/0211075 A1 | 8/2010 | Stone |
| 2010/0211173 A1 | 8/2010 | Bardos et al. |
| 2010/0249250 A1 | 9/2010 | Myers |
| 2010/0256677 A1* | 10/2010 | Albertorio et al. .............. 606/232 |
| 2010/0268273 A1 | 10/2010 | Albertorio et al. |
| 2010/0268275 A1 | 10/2010 | Stone et al. |
| 2010/0274355 A1 | 10/2010 | McGuire et al. |
| 2010/0274356 A1 | 10/2010 | Fening et al. |
| 2010/0292792 A1 | 11/2010 | Stone et al. |
| 2010/0305709 A1 | 12/2010 | Metzger et al. |
| 2010/0312341 A1 | 12/2010 | Kaiser et al. |
| 2010/0318188 A1 | 12/2010 | Linares |
| 2010/0324676 A1 | 12/2010 | Albertorio et al. |
| 2010/0331975 A1 | 12/2010 | Nissan et al. |
| 2011/0040380 A1 | 2/2011 | Schmieding et al. |
| 2011/0046734 A1 | 2/2011 | Tobis et al. |
| 2011/0054609 A1 | 3/2011 | Cook et al. |
| 2011/0087284 A1 | 4/2011 | Stone et al. |
| 2011/0098727 A1 | 4/2011 | Kaiser et al. |
| 2011/0112640 A1 | 5/2011 | Amis et al. |
| 2011/0112641 A1 | 5/2011 | Justin et al. |
| 2011/0118838 A1 | 5/2011 | Delli-Santi et al. |
| 2011/0137416 A1 | 6/2011 | Myers |
| 2011/0184227 A1 | 7/2011 | Altman et al. |
| 2011/0196432 A1 | 8/2011 | Griffis, III |
| 2011/0196490 A1 | 8/2011 | Gadikota et al. |
| 2011/0218625 A1 | 9/2011 | Berelsman et al. |
| 2011/0238179 A1 | 9/2011 | Laurencin et al. |
| 2011/0270278 A1 | 11/2011 | Overes et al. |
| 2011/0276137 A1 | 11/2011 | Seedhom et al. |
| 2011/0288635 A1 | 11/2011 | Miller et al. |
| 2011/0301707 A1 | 12/2011 | Buskirk et al. |
| 2011/0301708 A1 | 12/2011 | Stone et al. |
| 2012/0046746 A1 | 2/2012 | Konicek |
| 2012/0046747 A1 | 2/2012 | Justin et al. |
| 2012/0053630 A1 | 3/2012 | Denham et al. |
| 2012/0065732 A1 | 3/2012 | Roller et al. |
| 2012/0089143 A1 | 4/2012 | Martin et al. |
| 2012/0109299 A1 | 5/2012 | Li et al. |
| 2012/0123474 A1 | 5/2012 | Zajac et al. |

(56) References Cited

U.S. PATENT DOCUMENTS

| | | |
|---|---|---|
| 2012/0123541 A1 | 5/2012 | Albertorio et al. |
| 2012/0150297 A1 | 6/2012 | Denham et al. |
| 2012/0165938 A1 | 6/2012 | Denham et al. |
| 2012/0197271 A1 | 8/2012 | Astorino et al. |
| 2012/0296345 A1 | 11/2012 | Wack et al. |
| 2013/0023928 A1 | 1/2013 | Dreyfuss |

FOREIGN PATENT DOCUMENTS

| | | |
|---|---|---|
| EP | 0 440 991 | 8/1991 |
| EP | 1 108 401 | 6/2001 |
| EP | 1 707 127 | 10/2006 |
| WO | WO 2007/002561 | 1/2007 |
| WO | WO 2008/091690 | 7/2008 |

* cited by examiner

TENSIONABLE KNOTLESS ACROMIOCLAVICULAR REPAIRS AND CONSTRUCTS

CROSS-REFERENCE TO RELATED APPLICATIONS

This application claims the benefit of U.S. Provisional Application No. 61/510,727, filed Jul. 22, 2011, the entire disclosure of which is incorporated by reference herein.

FIELD OF THE INVENTION

The present invention relates to the field of surgery and, more particularly, to a joint or ligament reconstruction technique and associated fixation and reconstruction device.

BACKGROUND OF THE INVENTION

Acromioclavicular ("AC") joint dislocations are characterized by severe upward displacement of the lateral end of the clavicle relative to the acromium of the scapula. Surgery is recommended to reduce and internally fix the displacement, which could otherwise lead to a painful deformity and loss of function.

An exemplary method and apparatus for repairing AC joint dislocations is detailed, for example, in U.S. Patent Application Publication No. 2010/0125297, the disclosure of which is incorporated in its entirety herewith. The apparatus described therein comprises two buttons, or a button and a washer, that are joined by at least one strand of flexible material (for example, suture or tape, such as FiberTape®). Alternatively, in lieu of the two buttons, the apparatus may comprise a button/interference screw combination. A graft may be optionally attached to the apparatus for further insertion and positioning of the graft through the coracoid and the clavicle.

Current designs for AC repairs typically employ either a graft or strands of tape such as FiberTape®, and in some cases both graft and tape. Buttons on both ends, or a combination of a button and an interference fixation device (for example, an interference screw), are used to secure the graft to the coracoid and the clavicle.

BRIEF SUMMARY OF THE INVENTION

The present invention provides surgical constructs, systems and techniques for AC joint dislocation surgical repairs. The surgical systems comprise two fixation devices (for example, a button and an anchor) joined by strand of flexible material provided with a knotless, self-cinching, adjustable loop with two splices that attach to the two fixation devices. The knotless, adjustable loop/fixation devices allow for tensioning of the AC repair after the anchor implantation.

The present invention also provides an anchor/loop construct having an adjustable length and comprising an anchor pre-loaded with a knotless, self-locking, adjustable loop with two splices extending through the anchor. The anchor/suture construct may be employed in conjunction with a shuttling suture and/or driver to allow shuttling of the construct through the clavicle and coracoid, and to secure fixation of the anchor into or onto one of the clavicle and coracoid.

The present invention also provides a method of addressing both acute and chronic AC joint indications. The method of the present invention comprises the steps of: (i) providing a surgical construct including two fixation devices (i.e., a button and an anchor) joined by a flexible component (for example, suture); and (ii) engaging the surgical construct in or on the clavicle, and in or on the coracoid.

Other features and advantages of the present invention will become apparent from the following description of the invention which refers to the accompanying drawings.

DETAILED DESCRIPTION OF THE PREFERRED EMBODIMENTS

Figure 1:
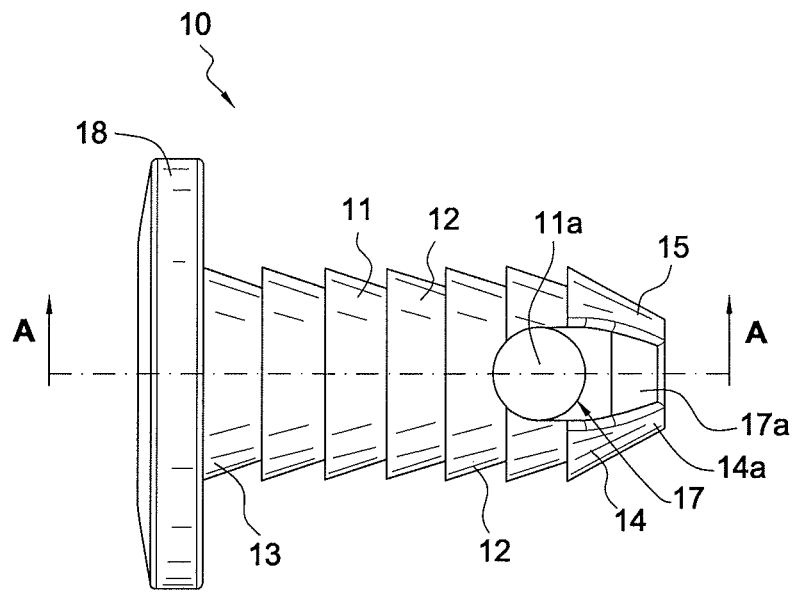
FIG. 1 illustrates a side view of a suture anchor of a surgical construct of the present invention (used in conjunction with a button).

The present invention provides techniques and reconstruction systems for repairing AC joint dislocations. The reconstruction systems of the present invention comprise two fixation devices (i.e., a button and an anchor) optionally joined by a biologic component (for example, a graft such as an allograft or autograft) and at least a strand of flexible material (for example, a high strength suture such as FiberWire® suture, sold by Arthrex, Inc. of Naples, Fla., which is disclosed and claimed in U.S. Pat. No. 6,716,234, the entire disclosure of which is incorporated herein by reference). Typically the suture will be UHWMPE suture without a core to permit ease of splicing.

The anchor has a specific structural configuration, i.e., with a cannulated T-shaped body having a flange at the proximal end and a transversal eyelet defining a plurality of longitudinally-extending channels at the distal end. The specific configuration of the anchor allows a knotless, self-locking, adjustable loop with two splices to attach to the anchor and to foam, therefore, a knotless, adjustable suture loop/anchor construct that allows for tensioning of the AC repair after the anchor implantation.

The use of a button and an anchor is advantageous over the use of two buttons (or a button and a washer) as it eliminates the knot stack on top of the buttons and leaves a smooth surface on top of the clavicle (i.e., leaves a smooth metal button-like protrusion on top of the clavicle). The use of a button and an anchor is also advantageous over the use of a button/interference screw combination, as the button/anchor combination allows the ability to tension the suture after implantation (i.e., allows for a knotless AC repair as well as for tensioning after implantation). Another advantage of a button and anchor construct over a two button construct is the improved stability of the construct. The anchor prevents movement along the clavicle bone which may occur with the use of a second button.

As described in more detail below, the anchor is preloaded with a flexible strand (for example, suture) that contains two suture splices that are self-cinching (similar to the suture splices used in adjustable suture button/loop construct described in U.S. Patent Application Publication Nos. 2010/

0268273 and 2010/0256677, sold by Arthrex, Inc. under the tradename ACL TightRope™). The lead loops of the suture are weaved through a suture loop (e.g., an Arthrex FiberLink™) located at the tip of the anchor. The remaining suture and splices are weaved on the opposite side of the anchor and are contained in a driver before implantation.

An exemplary method of AC repair comprises inter alia the steps of: providing an anchor/suture loop construct including an anchor and a flexible self-cinching construct provided with a self-cinching, adjustable, continuous suture loop with two splices and also including two lead loops attached to a shuttle loop; securing the anchor/suture loop construct to a driver and containing the adjustable, continuous suture loop and two splices within the driver; passing the two lead loops and the shuttle loop through holes/tunnels formed into the clavicle and coracoid; securing the anchor into the clavicle tunnel; pulling the shuttle loop to shuttle the flexible self-cinching construct through both clavicle and coracoid tunnels; removing the shuttle loop and attaching the two unattached lead loops to a fixation device; pulling on the free suture ends attached to the adjustable, continuous suture loop with two splices to secure the fixation device on the coracoid and to shorten the length of the flexible self-cinching construct; tightening the fixation device against the coracoid; and cutting the free suture ends.

Figure 2:
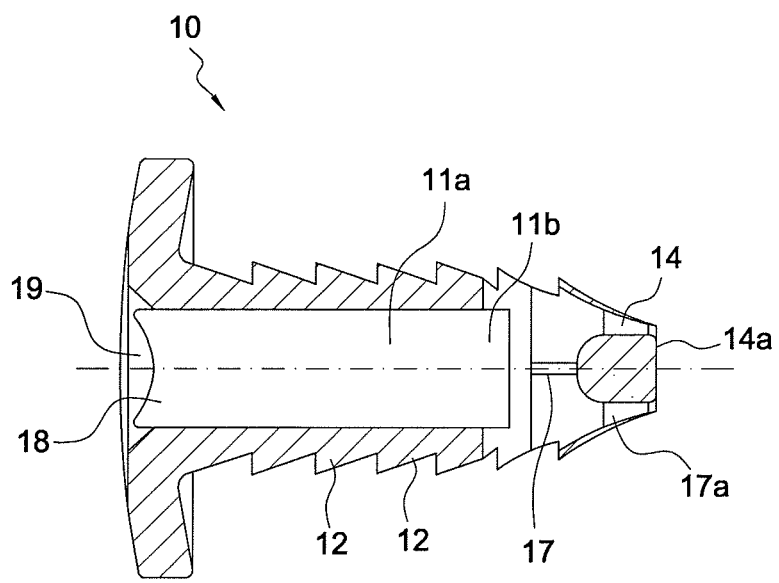
FIG. 2 illustrates a cross-sectional view of the suture anchor of FIG. 1, taken along line A-A.

Referring now to the drawings, where like elements are designated by like reference numerals, FIGS. 1 and 2 illustrate a side and cross-sectional views of suture anchor 10 of the present invention. Anchor 10 has a T-shape configuration. Anchor 10 is provided with body 11 having a cylindrical configuration (having a constant outer diameter) with a longitudinal axis 11a, a proximal end 13 and a distal end 15, and a plurality of ribs 12 extending circumferentially around it.

A flange 18 (having an exemplary round cross-section and a annulations) is provided at the proximal end 13 of body 11. Flange 18 has a diameter about twice the outer diameter of body 11 to allow secure engagement of the anchor 10 onto the base of the clavicle (or within the clavicle) as detailed below. Cannulation 11b (FIG. 2) extends along the body 11 and the flange 18 to allow passage of flexible suture loop constructs, as also detailed below.

Conical tip 14 is provided at the distal end 15 of the anchor 10 and contains eyelet 17 (bore 17) extending in a direction about perpendicular to the longitudinal axis 11a. Eyelet 17 communicates with the outer surfaces of the tip 14 and with most distal surface 14a of the tip 14 through a plurality of channels/holes 17a, 17b which extend about parallel to the longitudinal axis 11a. Channels/holes 17a, 17b are positioned opposite to each other and are symmetrically located relative to the longitudinal axis 11a, to allow loops of flexible strand 20 to pass and slide therethrough as detailed below. The position and size of the channels 17a, 17b may be determined according to the characteristics of the arthroscopic procedure, and the need to precisely orientate the eyelet during anchor insertion to optimize suture sliding characteristics.

Anchor 10 may be a screw-in anchor or a push-in style anchor. Anchor 10 may be formed of metal, biocompatible plastic such as PEEK or a bioabsorbable PLLA material. A socket 19 at the proximal end 13 of the anchor 10 is configured to securely engage a tip of a driver (such as driver 15 of FIG. 4). In an exemplary embodiment only, the socket 19 of the anchor 10 has a rectangular cross-section to allow secure engagement of the tip of driver 15, also provided with a complementary, rectangular cross-section. The socket of the anchor 10 may have, however, any shape adapted to receive a driver tip for tapping or screw-in style anchors.

Figure 3:
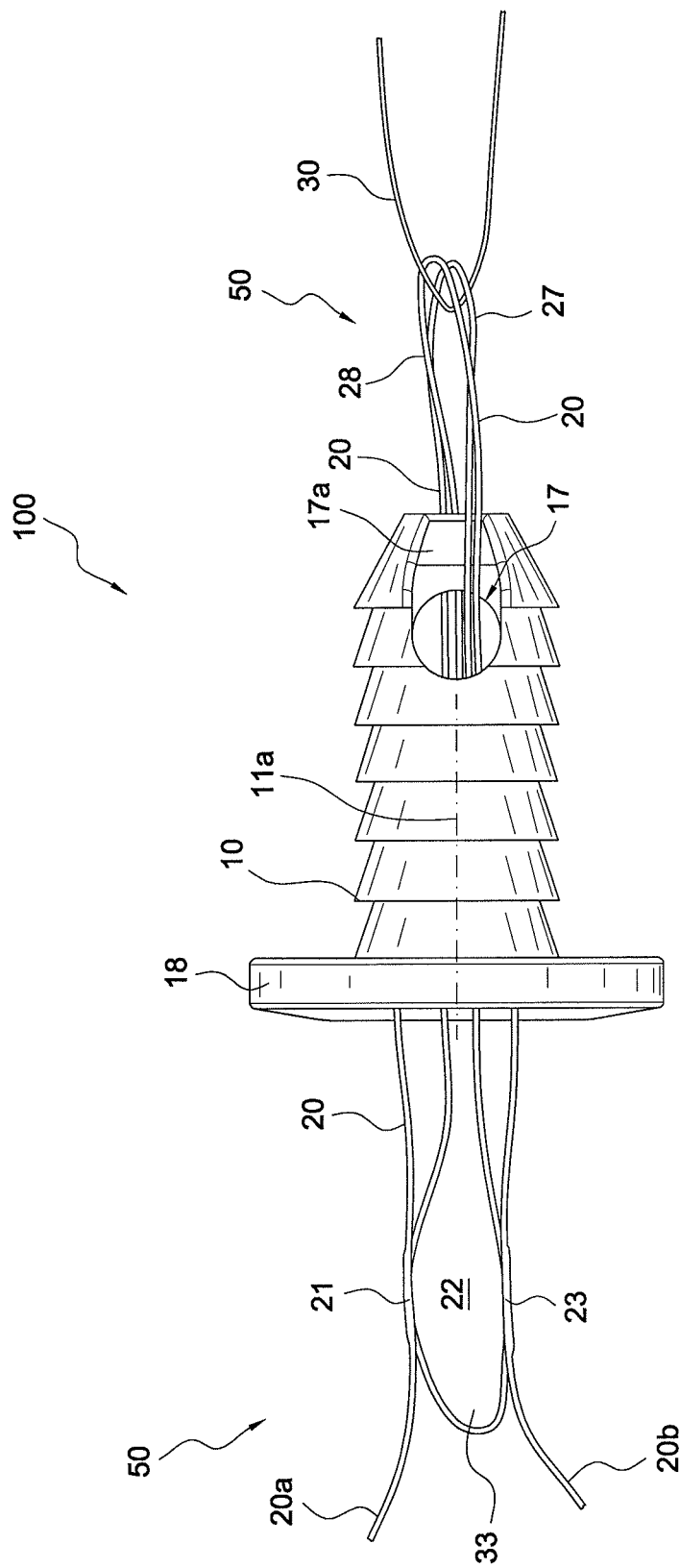
FIG. 3 is a side view of a knotless, self-locking, adjustable construct of the present invention (with the suture anchor of FIG. 1 and with an adjustable, self-locking, knotless loop of flexible material attached to the anchor).

Reference is now made to FIG. 3 which illustrates the anchor 10 of FIGS. 1 and 2 assembled with suture construct 50 formed of flexible material 20 (suture 20) and shuttle/pull suture 30 (FiberLink™ 30 or loop 30). Suture construct 50 is formed of suture 20 having one adjustable, self-cinching loop 22, two suture splices 21, 23 (self-cinching splices) and two lead loops 27, 28. Each of lead loops 27, 28 of the suture 20 has a fixed diameter (preferably, the diameters of lead loops 27, 28 are about equal). Lead loops 27, 28 of the suture 20 are passed through the pull or shuttle suture 30 located at the tip (eyelet 17) of the anchor 10. The remaining suture and splices 21, 23 are passed on the opposite side of the anchor 10 and are contained in driver 15 before implantation (i.e., the remaining suture and splices 21, 23 extend through the whole length of the cannulated driver 15 including the whole length of the cannulated handle of the driver 15).

Integrated system 100 is shown in FIG. 3. Integrated system 100 comprises anchor 10 and suture construct 50 formed of suture 20 together with loops 22, 27 and 28 (which are passed through eyelet 17 at the tip of the anchor and cannulation 11b of the anchor 10).

FIG. 3 also illustrates a shuttle/pull suture 30 (for example, a FiberLink™) or a nitinol loop which is attached to the suture construct 50 of integrated system 100, to allow shuttling of the suture construct through both tunnels in clavicle and coracoid and out of the exit portal, as detailed below. The FiberLink™ is attached to the two lead loops 27, 28 of suture 20. Free suture ends 25, 26 are exposed outside the anchor to allow tensioning after implantation.

Suture construct 50 comprises knotless, adjustable, flexible loop 22 which has an adjustable length and is attached to the suture anchor 10. Details and the formation of the suture splices 21, 23 of the knotless, self-locking, adjustable construct 50 are set forth, for example, in U.S. Patent Publication Nos. 2010/0268273 and 2010/025667, the disclosure of both of which are incorporated by reference in their entirety herewith. Details on assembling the construct 100 of the present invention (i.e., integrated system 100 consisting of suture construct 50 and suture anchor 10) are set forth below with reference to FIGS. 8-21.

FIGS. 4-7 illustrate the system 100 of FIG. 3 (with suture construct 50 attached to suture anchor 10) employed in an exemplary method of AC joint reconstruction according to an embodiment of the present invention. As detailed below, system 100 will be used in conjunction with an exemplary fixation device, such as button 60, for example. However, the invention is not limited to this exemplary embodiment and contemplates the use of any other fixation device, for example, any type of anchor or implant or screw that allows attachment of the suture construct 50 to the coracoid.

An exemplary method of AC joint repair of the present invention comprises inter alia the steps of: (i) providing a surgical construct including two fixation devices 10, 60 (i.e., a button 60 and an anchor 10) joined by a self-cinching, adjustable flexible construct formed of a flexible component 20 (for example, suture) provided with an adjustable, flexible loop 22 and two splice regions 21, 23 (self-cinching splices 21, 23); and (ii) engaging the surgical construct in or on the clavicle, and in or on the coracoid.

Figure 4:
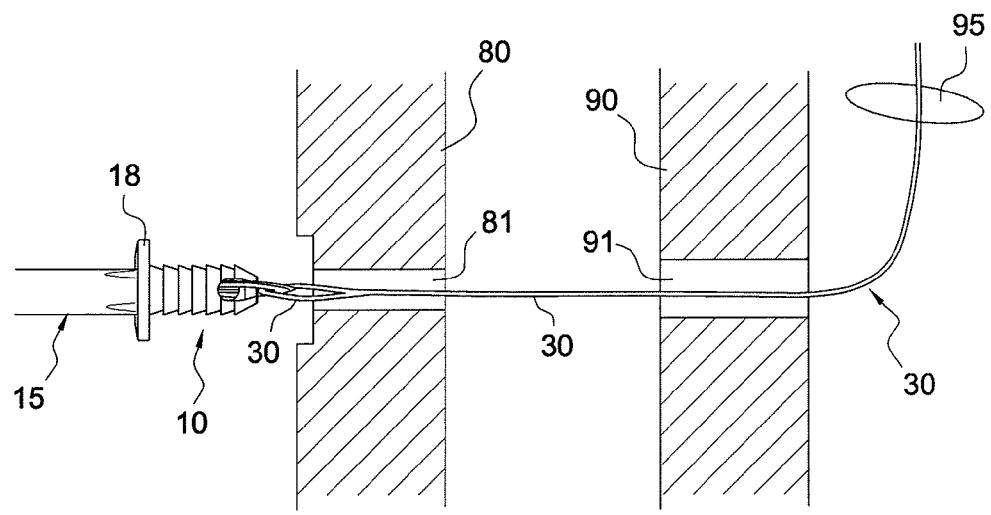
FIGS. 4-7 illustrate subsequent steps of a method of AC repair using the construct of FIG. 3, and according to an exemplary embodiment of the present invention.

FIG. 4: Bone tunnels 81, 91 (through holes 81, 91) are drilled through clavicle 80 and coracoid 90, respectively. A guide pin such as a 2.4 mm guide pin (not shown) may be used for the formation of tunnels 81, 91. The clavicle 80 may be drilled over the guide pin with an appropriate size drill to create a hole for anchor 10. Optionally, a countersunk hole is drilled in the cortical bone of the clavicle, as shown.

Figure 5:
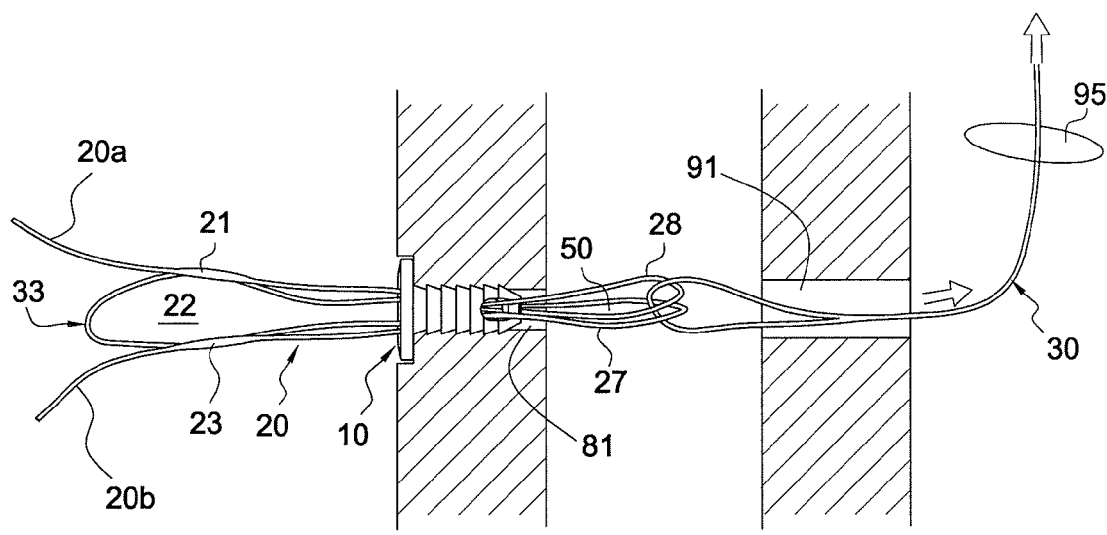

Through suture passing methods, shuttle/loop 30 (such as FiberLink™ 30) is passed through both holes 81, 91 and out the exit portal 95. As shown in FIGS. 4 and 5, the FiberLink™ 30 is not attached to the anchor 10 but rather to the two lead loops 27, 28 of the construct 50. Anchor 10 is shown engaged by driver 15 in FIG. 4.

FIG. 5: Anchor 10 is tapped or screwed in clavicle tunnel 81. The driver 15 is then removed. Construct 50 remains in place. Splices 21, 23 are self-cinching and have an exemplary length of about 0.75 inches. FiberLink™ 30 is pulled to shuttle the construct 50 through both holes 81, 91 and out of the exit portal 95.

Figure 6:
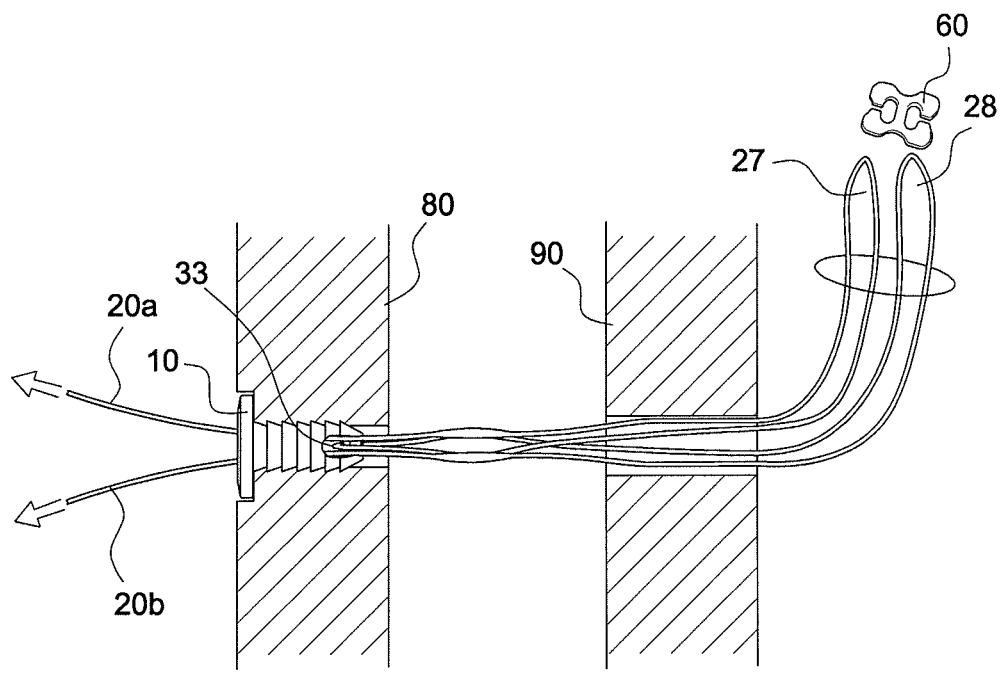

FIG. 6: FiberLink™ 30 is cut, leaving the two lead loops 27, 28 of suture 20 outside the portal. Slotted button 60 (having a dog bone configuration, for example) is used to attach suture loops 27, 28.

Figure 7:
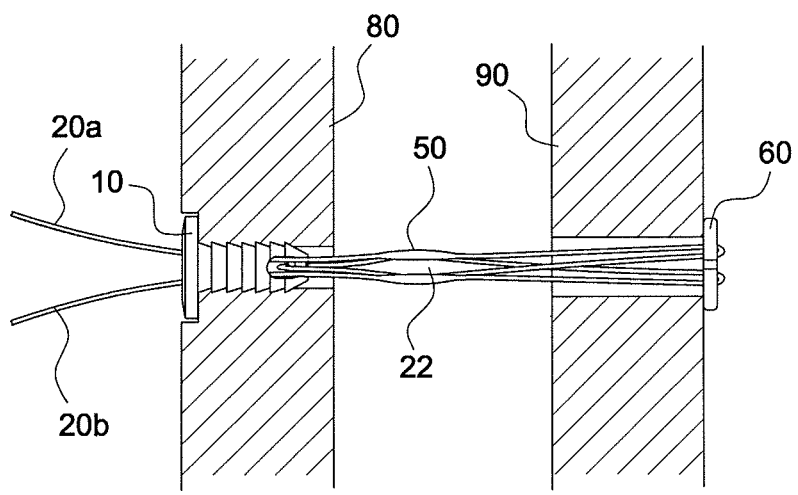

FIG. 7: Free ends 20a, 20b of suture 20 are pulled, pulling suture button 60 back towards the hole 91. Once button 60 hits the bone (coracoid) 90, tension between the button 60 and the tip of the anchor 10 increases. Ideally, "hook" 33 on the suture 20 should rest on the channel cut on the tip of the anchor 10. The free ends 20a, 20b of suture are cut once button 60 is tightened against the bone 90. The construct 100 works even if not properly aligned.

FIGS. 8-21 illustrate subsequent steps of a method of assembling system 100 of FIG. 3 (with suture construct 50 attached to suture anchor 10).

Figure 8:
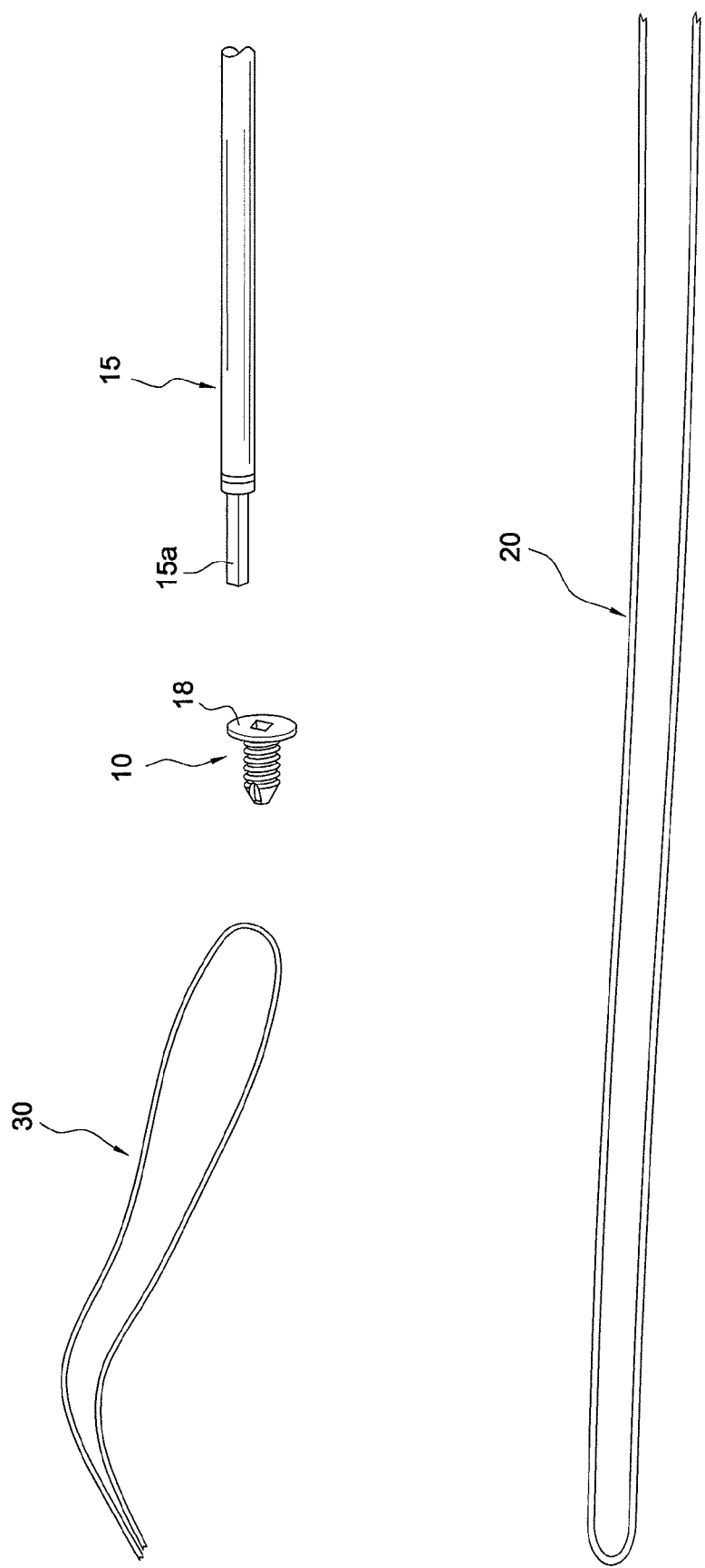
FIGS. 8-21 illustrate subsequent steps of a method of assembling the suture to the anchor, to create the suture and anchor construct of the present invention.

FIG. 8: The materials for suture and anchor construct 100 are anchor 10, driver 15, flexible strand 20 (exemplary single strand UHMWPE suture 20) and shuttle/pull strand 30 (exemplary FiberLink™ 30).

Figure 9:
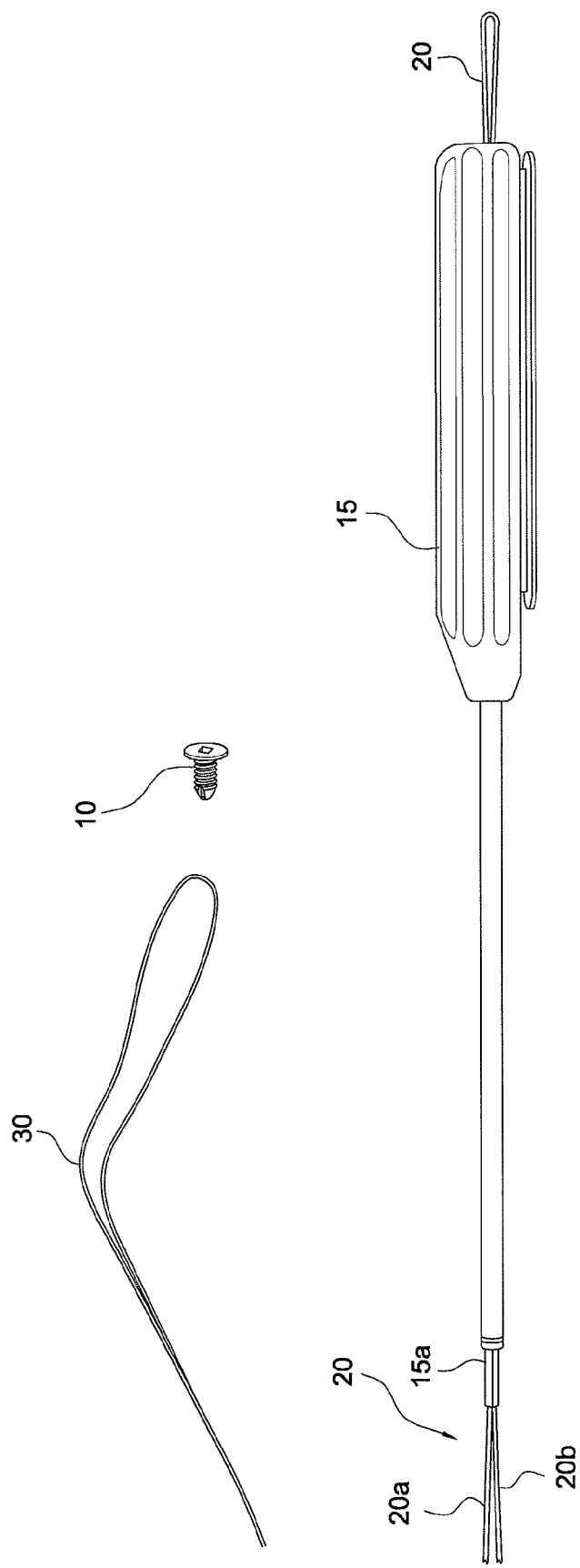

FIG. 9: Suture 20 is folded in half and is pulled through the driver 15 with a suture passing instrument.

Figure 10:
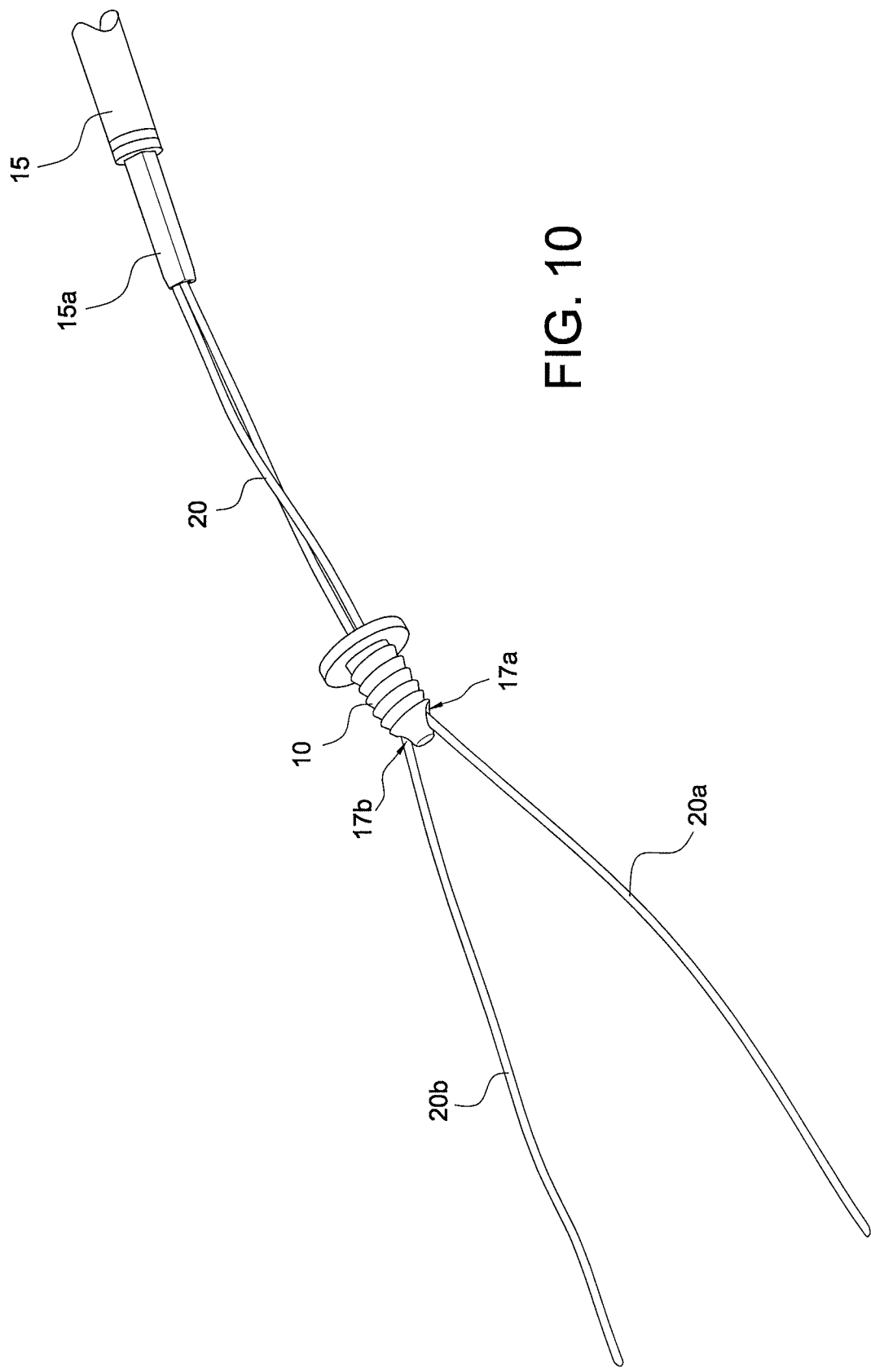

FIG. 10: Each end 20a, 20b of the suture 20 is pulled through anchor 10 and through opposite channels/holes 17a, 17b of the eyelet 17 at the tip 14 of the anchor 10.

Figure 11:
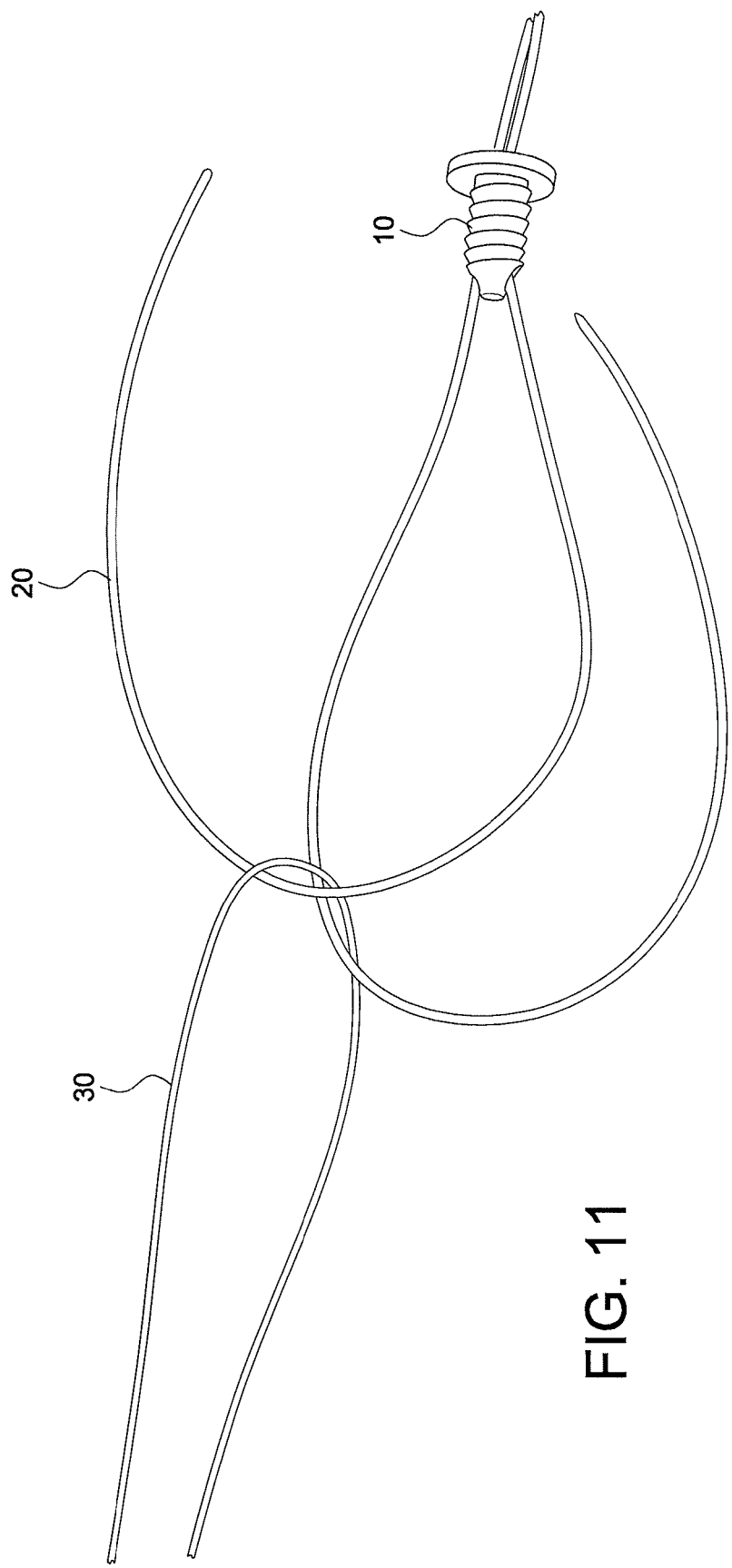

FIG. 11: The free ends 20a, 20b of suture 20 are passed through the loop of the FiberLink™ 30.

Figure 12:
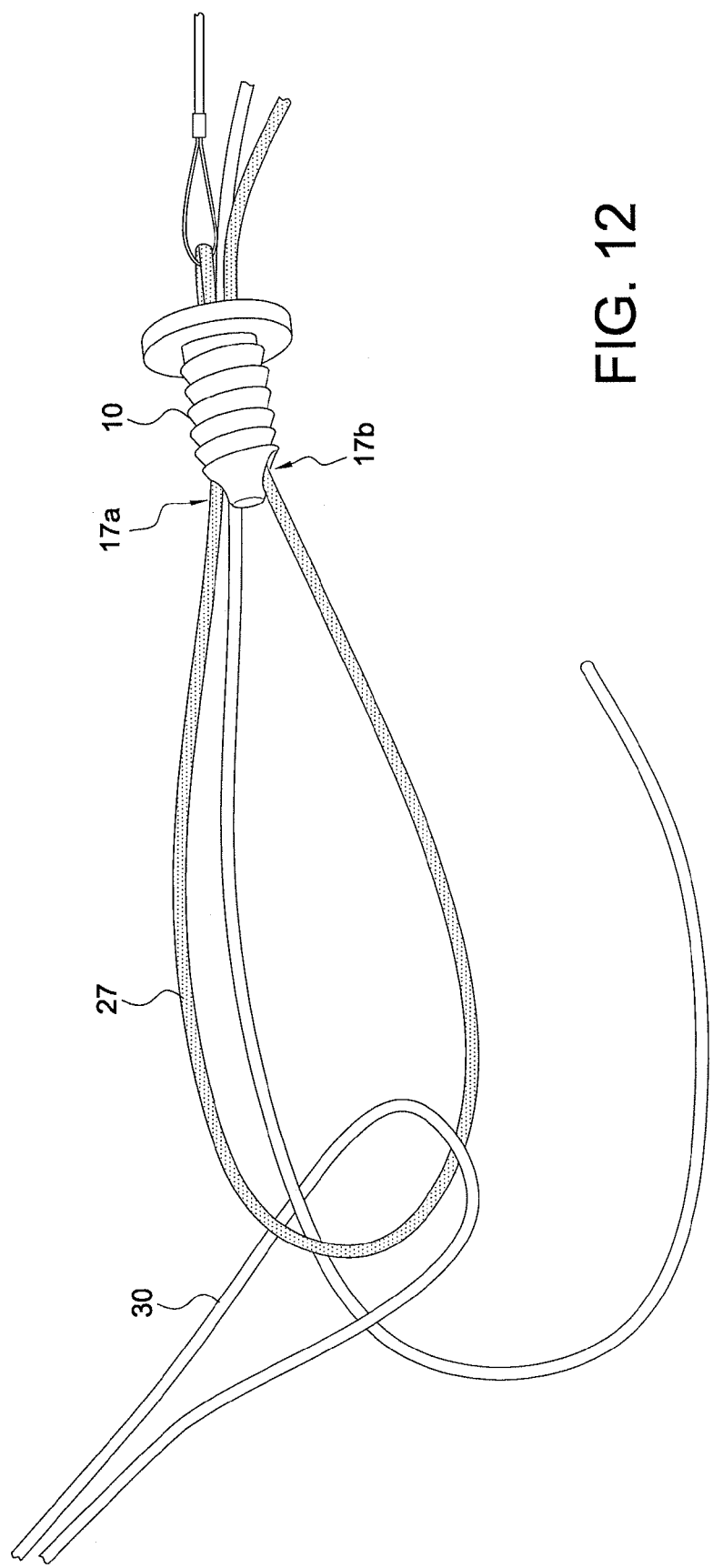
Figure 13:
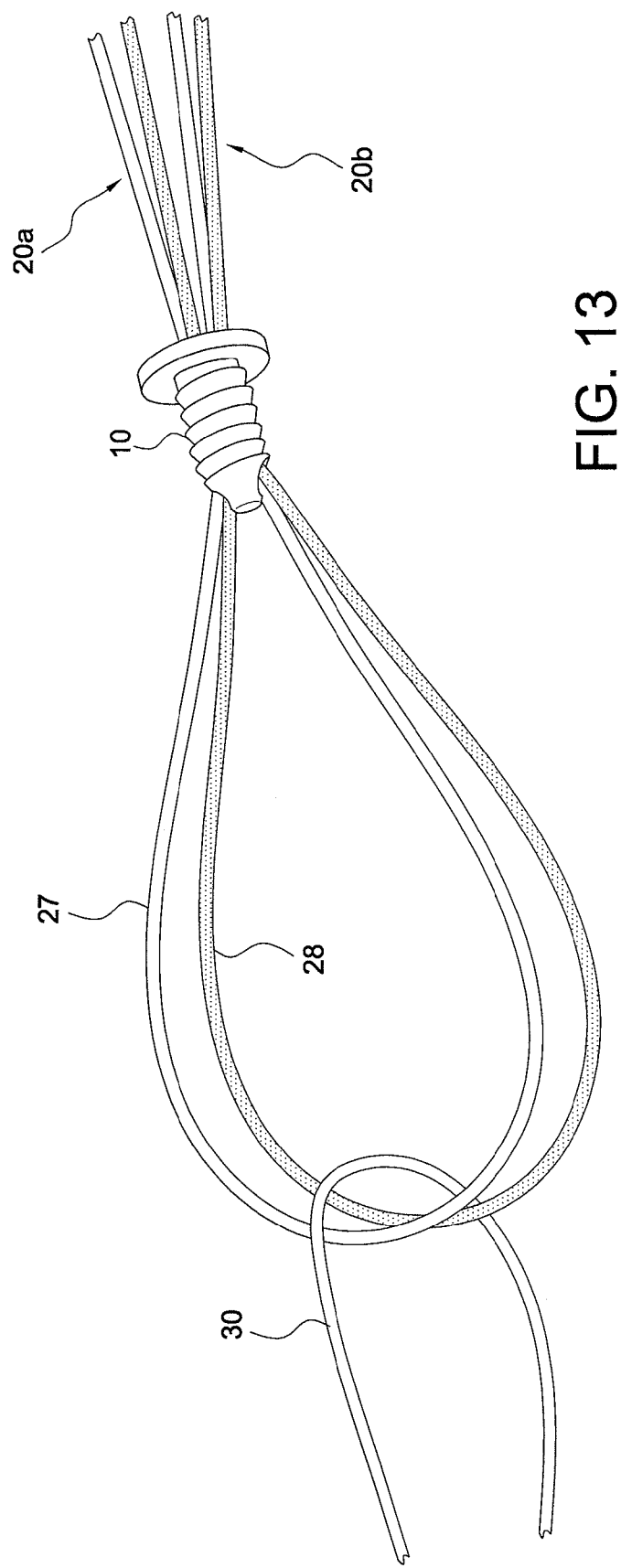

FIGS. 12 and 13: Using a suture passing instrument, the free ends 20a, 20b of suture 20 are passed through opposite eyelet holes 17a, 17b (of eyelet 17) from which they were previously passed.

Figure 14:
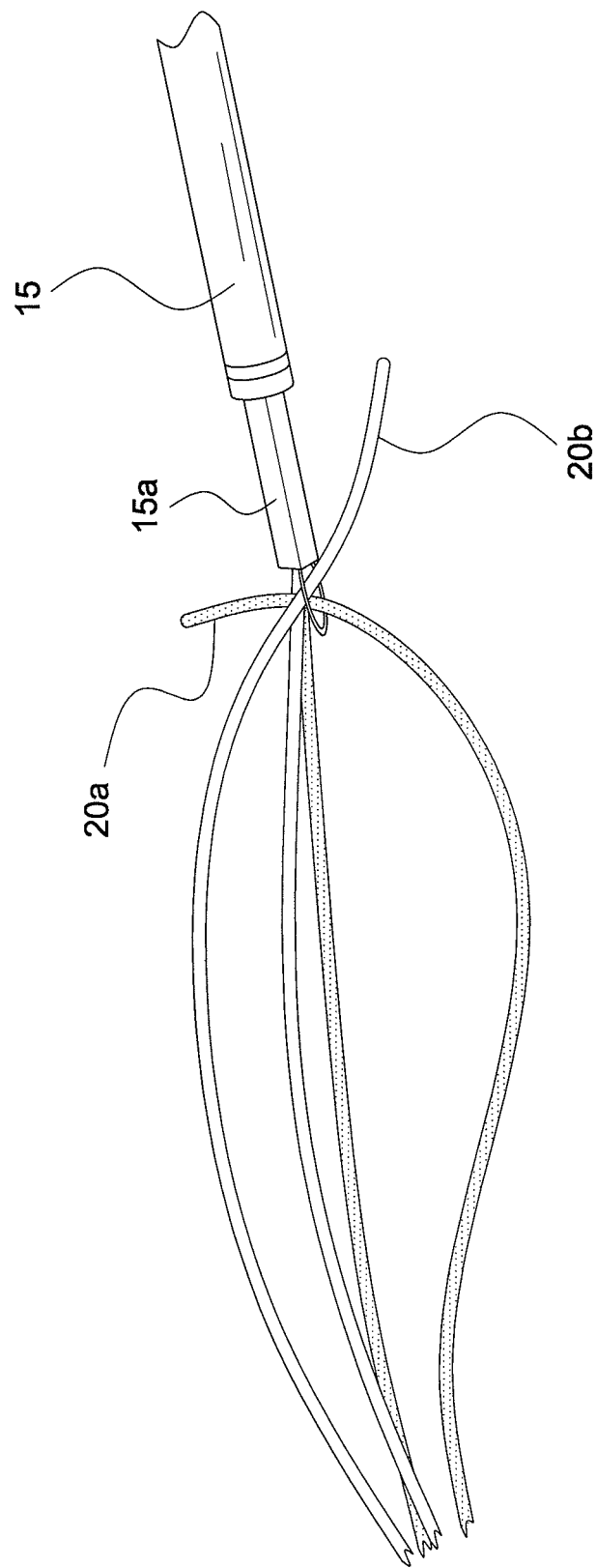
Figure 15:
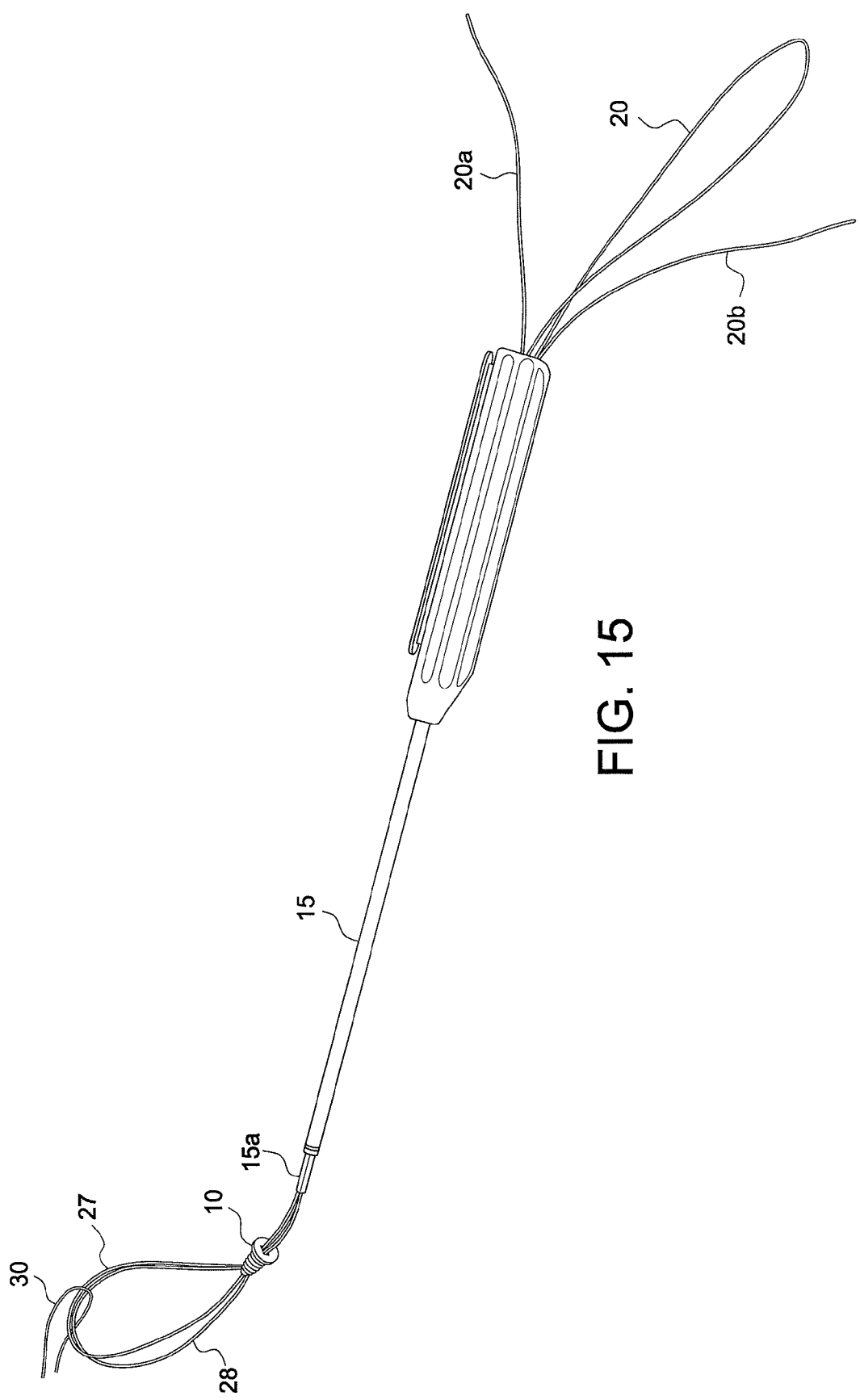

FIGS. 14 and 15: Using a suture passing instrument, both free ends 20a, 20b of suture 20 are passed through the driver 15.

Figure 16:
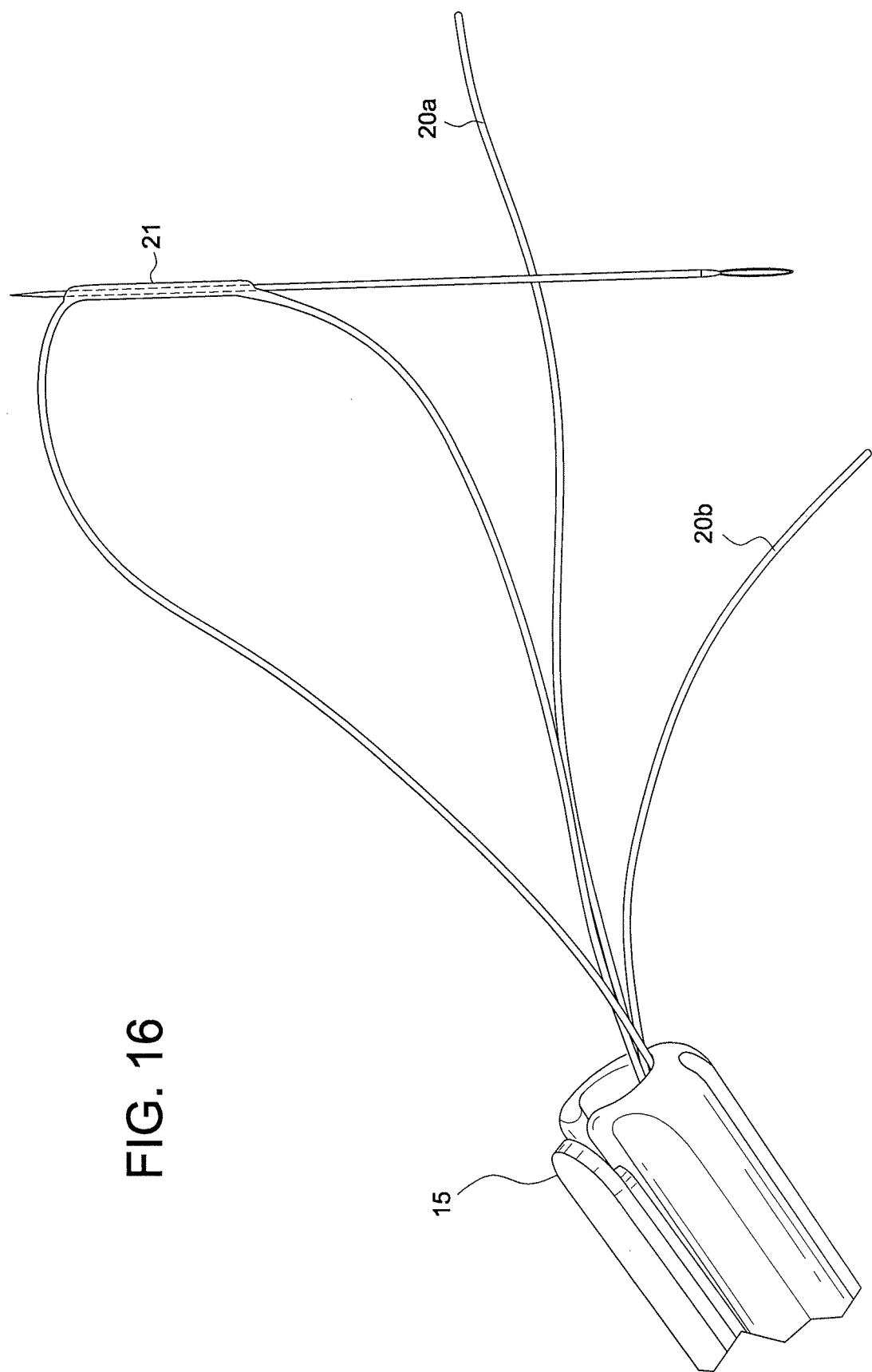

FIG. 16: Splices 21, 23 are formed in the same fashion as the ACL TightRope™.

Figure 17:
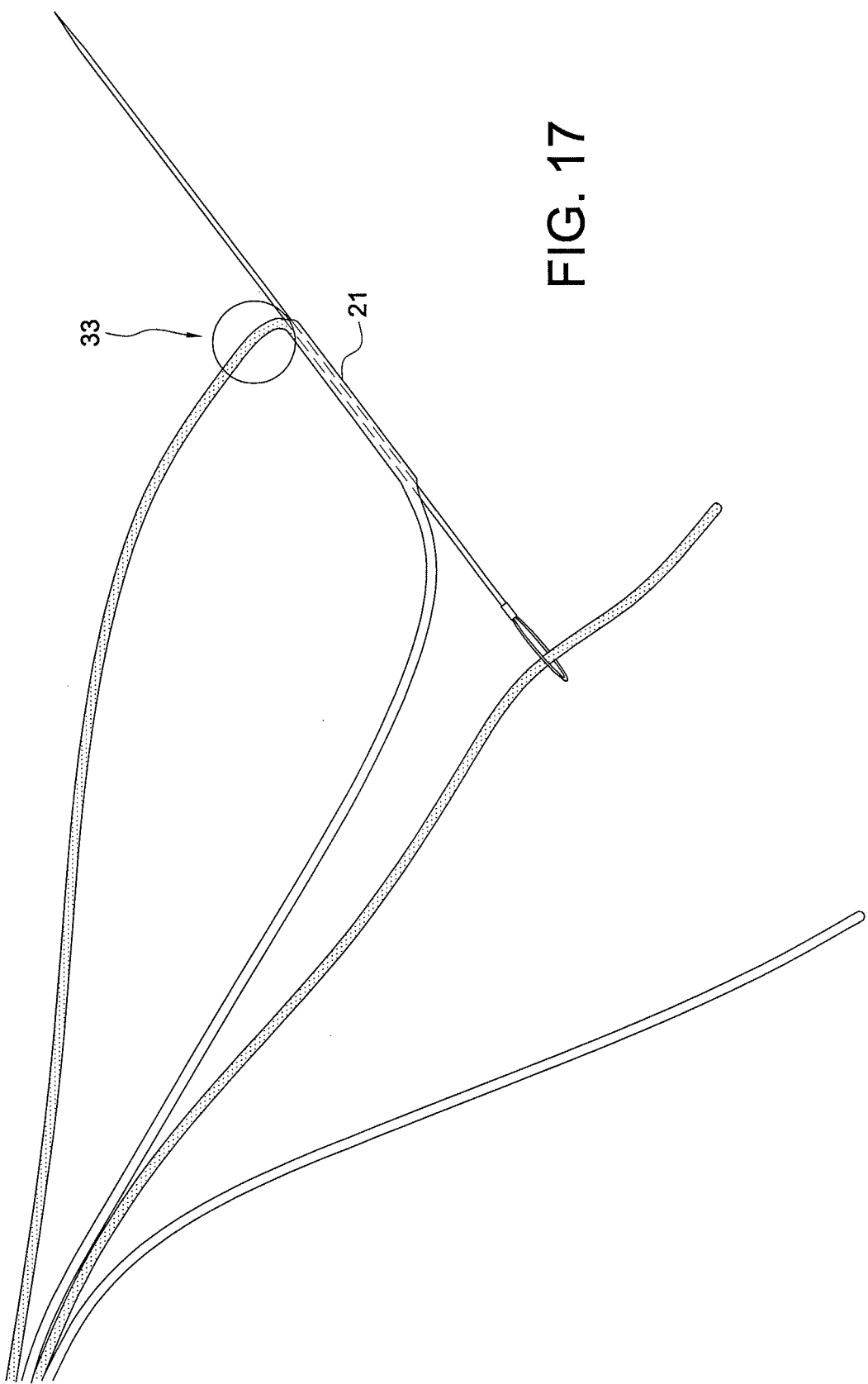
Figure 18:
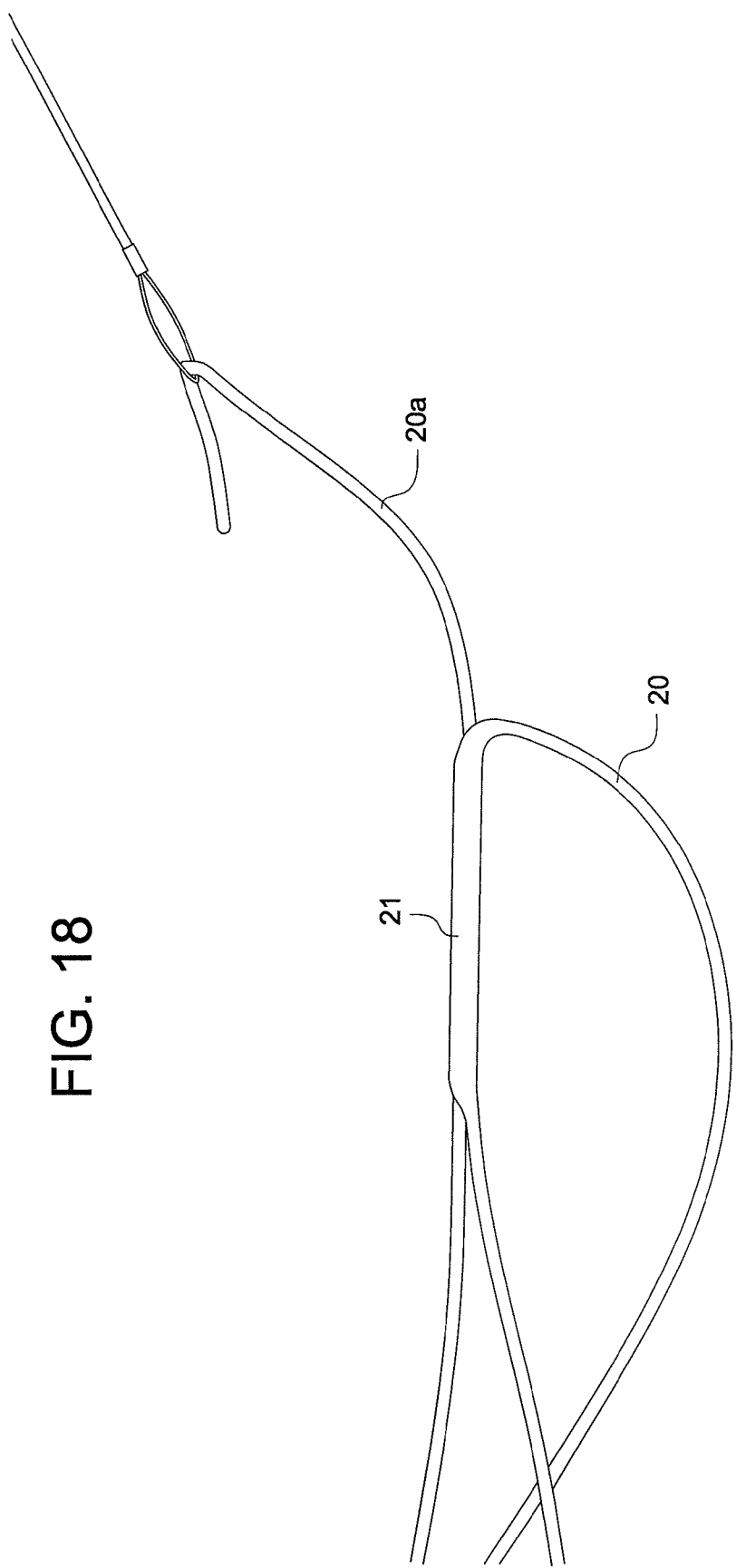

FIGS. 17 and 18: Suture 20 is spliced through opposing side of suture. The "side" of suture is split at "hook" or fold 33. The first finished splice 21 is shown in FIG. 18.

Figure 19:
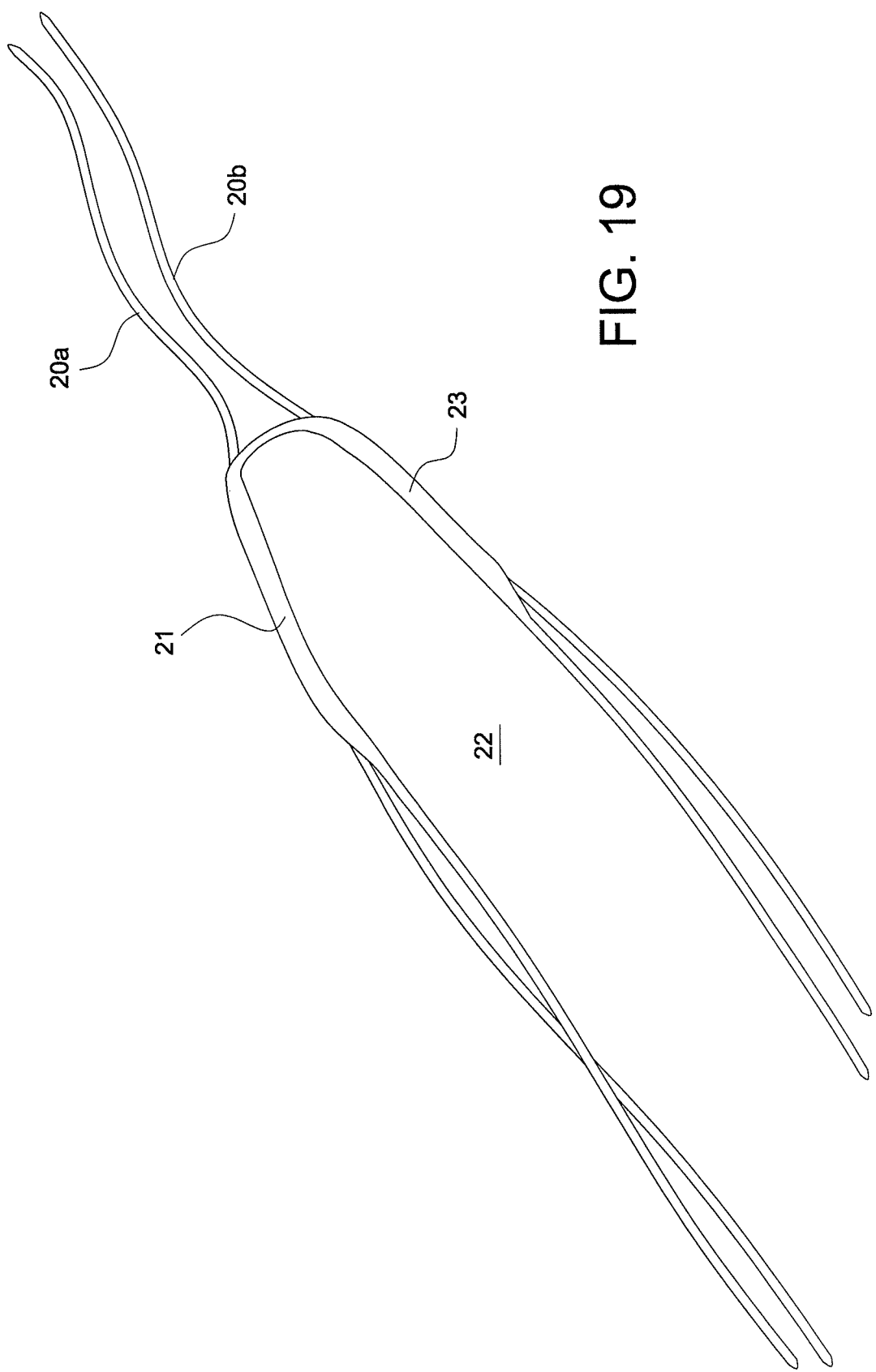

FIG. 19: Same splice is done for the other free end (to form second splice 23), leaving about 2-5 mm hook.

Figure 20:
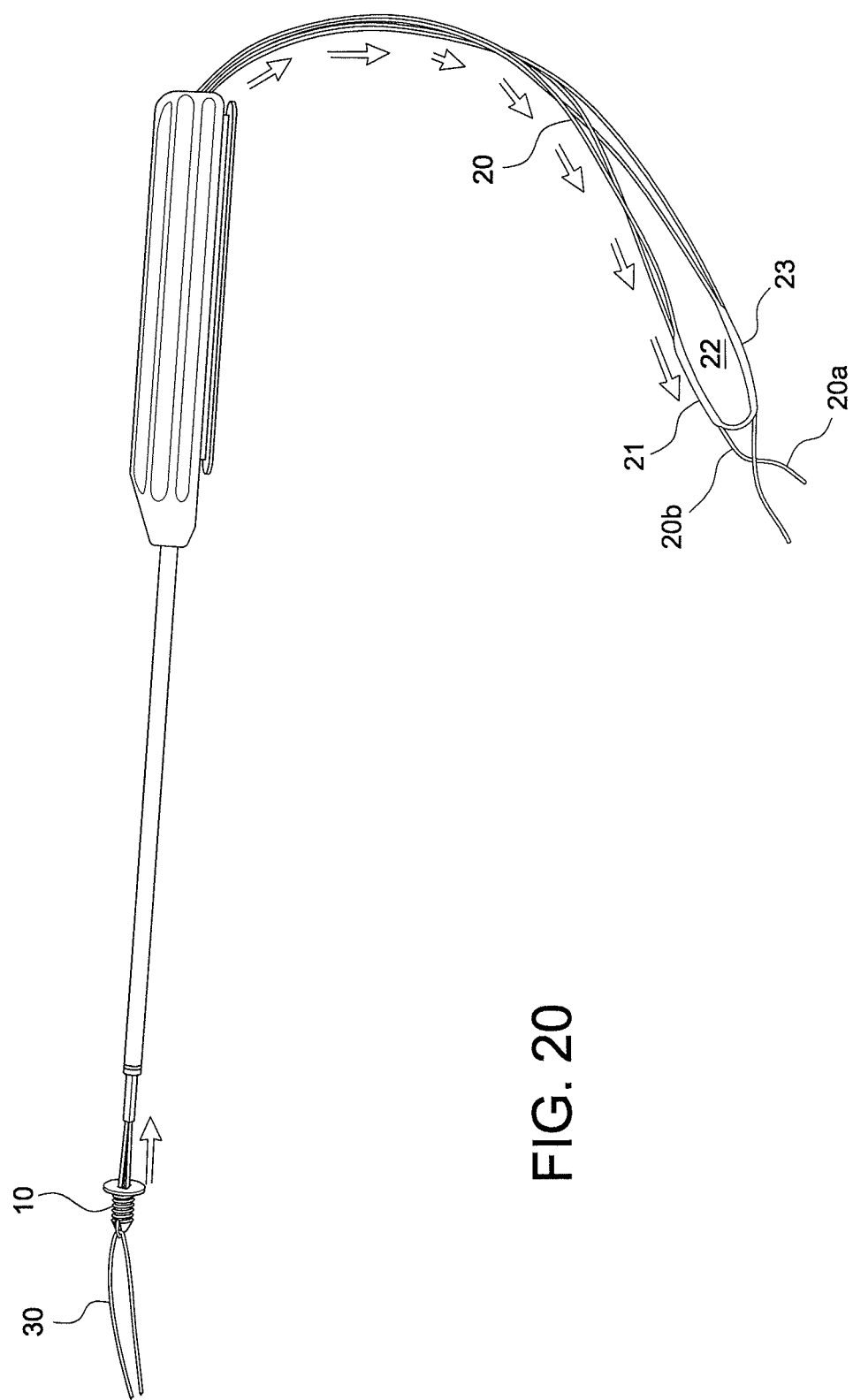

FIG. 20: Slack is pulled through the driver 15 by pulling on the hook or fold. The slack is released through the free ends 20a, 20b so that the strands going from the hook to the anchor are all even. The free ends 20a, 20b are then cut to be even. The slack is then pulled further until the anchor 10 seats on the driver 15 and the FiberLink™ 30 is pulled towards the tip of the anchor 10.

Figure 21:
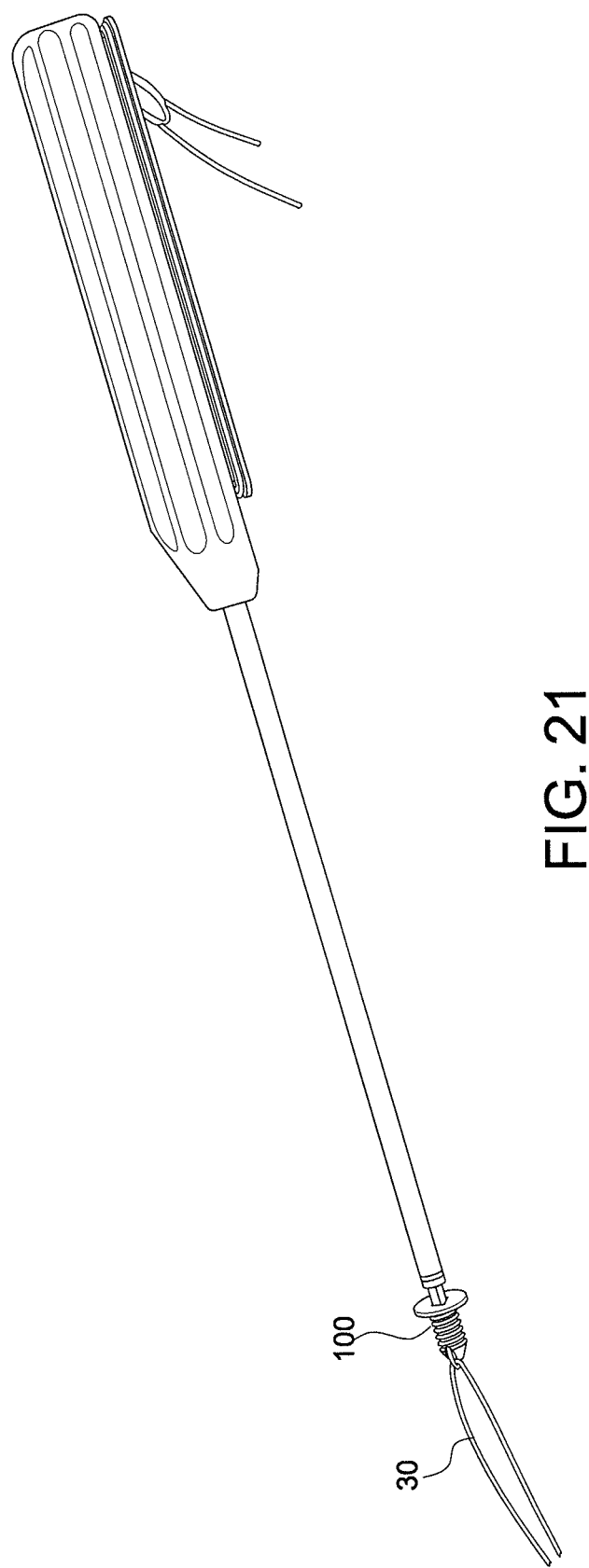

FIG. 21: Final assembly 100 is ready for use.

Splice areas 21, 23 and loop 22 are formed—at least in part—in a manner similar to the suture splices used in adjustable suture button/loop construct described in U.S. Patent Application Publication Nos. 2010/0256677 and 2010/0268273, the disclosures of which are incorporated by reference herein (and sold by Arthrex under the tradename ACL TightRope™).

At least one of the flexible strands 20, 30 forming construct 50 may be a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

The flexible strands of the present invention may also be formed of a stiff material, or combination of stiff and flexible materials, depending on the intended application. The strands may be also coated and/or provided in different colors. The knotless anchor of the present invention can be used with any type of flexible material or suture that forms a splice and a loop.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is to be limited not by the specific disclosure herein, but only by the appended claims.

What is claimed is:

1. A knotless system for acromioclavicular surgical repairs, comprising:

a fixation device comprising a cannulated anchor body having a cylindrical configuration with a longitudinal axis, a proximal end and a distal end, an outer surface, a tip provided at the distal end and a flange located at a most proximal end, the fixation device further comprising a transversal eyelet provided at the tip at the distal end and extending in a direction perpendicular to the longitudinal axis, the transversal eyelet communicating with outer surfaces of the tip and with a most distal surface of the tip through a pair of longitudinal-extending outer channels, the longitudinally-extending outer channels extending from the transversal eyelet and to the outer surface of the anchor body; and a knotless suture construct pre-loaded on the fixation device, the knotless suture construct comprising a flexible strand, a flexible continuous loop with an adjustable diameter formed in the flexible strand, and two splice regions formed within the flexible continuous loop, the knotless suture construct extending through the cannulated anchor body and the eyelet, and with the flexible strand being further threaded through the eyelet to form two flexible loops with fixed diameter, the two flexible loops with fixed diameter passing and sliding through the eyelet and the longitudinally-extending outer channels.

2. The knotless system of claim 1, wherein the fixation device is an anchor with a T-shape configuration.

3. The knotless system of claim 1, wherein the flange has a diameter about twice the diameter of the cannulated anchor body.

4. The knotless system of claim 1, wherein the cannulated anchor body has an opening at a most proximal end configured to receive a driver head for driving the fixation device.

5. The knotless system of claim 1, wherein the cannulated anchor body is provided with a plurality of circumferential ribs extending from an outer surface of the anchor body.

6. The knotless system of claim 1, wherein the flexible strand is a suture formed of ultrahigh molecular weight polyethylene.

7. The knotless system of claim 1, further comprising a pull suture threaded through the two loops with a fixed diameter, to shuttle the two loops through tunnels formed in a clavicle and a coracoid.

8. The knotless system of claim 1, wherein the flexible continuous loop with an adjustable diameter comprises two flexible limbs extending from the flexible continuous loop.

* * * * *